(12) United States Patent
Cha et al.

(10) Patent No.: US 6,346,533 B1
(45) Date of Patent: Feb. 12, 2002

(54) INTRACONAZOLE EXHIBITING AN IMPROVED SOLUBILITY, A METHOD OF PREPARING THE SAME AND A PHARMACEUTICAL COMPOSITION FOR ORAL ADMINISTRATION COMPRISING THE SAME

(75) Inventors: Bong-Jin Cha, Kyungki-do; Jun-Gyo Oh, Seoul; Su-Eon Kim, Kyungki-do, all of (KR)

(73) Assignee: Dong-A Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 09/445,886

(22) PCT Filed: Jun. 16, 1998

(86) PCT No.: PCT/KR98/00164

§ 371 Date: Dec. 14, 1999

§ 102(e) Date: Dec. 14, 1999

(87) PCT Pub. No.: WO98/57967

PCT Pub. Date: Dec. 23, 1998

(30) Foreign Application Priority Data

Jun. 16, 1997 (KR) .............................. 97-24938

(51) Int. Cl.⁷ ........................ A61K 31/495; A61K 9/14; A61K 25/00; A61K 31/335; A61K 31/41

(52) U.S. Cl. .................. 514/254.05; 424/405; 424/489; 514/247; 514/252.1; 514/252.11; 514/252.12; 514/252.13; 514/254.07; 514/254.1; 514/255.05; 514/383; 514/384; 514/449; 514/461; 514/463; 514/951

(58) Field of Search ................................ 424/489, 405; 514/247, 252.1, 252.11, 254.07, 252.12, 252.13, 254.1, 255.05, 383, 384, 449, 461, 463, 951

(56) References Cited

U.S. PATENT DOCUMENTS

| | | | |
|---|---|---|---|
| 4,267,179 A | 5/1981 | Heeres et al. ........... | 514/254.07 |
| 4,368,200 A | 1/1983 | Heeres et al. ........... | 514/254.07 |
| 4,490,530 A | 12/1984 | Heeres et al. ................ | 544/370 |
| 4,764,604 A | 8/1988 | Mëller ........................ | 536/103 |
| 4,870,060 A | 9/1989 | Müller ........................ | 514/58 |
| 5,474,997 A | 12/1995 | Gray et al. ............. | 514/254.07 |
| 5,633,015 A | 5/1997 | Gilis et al. ................... | 424/490 |
| 5,686,133 A * | 11/1997 | Amidon et al. ............. | 427/2.22 |
| 5,750,147 A * | 5/1998 | Kantor ........................ | 424/491 |
| 5,776,495 A * | 7/1998 | Duclos et al. ............... | 424/455 |
| 2001/0007678 A1 * | 7/2001 | Baert et al. ................. | 424/464 |

FOREIGN PATENT DOCUMENTS

| | | |
|---|---|---|
| EP | 0 006 711 | 1/1980 |
| EP | 0 147 171 A2 * | 7/1983 |
| EP | 0 197 571 | 10/1986 |
| EP | 0 147 171 | 6/1987 |
| WO | WO 94/05263 * | 3/1994 |
| WO | WO 94/16 700 | 8/1994 |
| WO | WO 94/16 733 | 8/1994 |
| WO | WO 95/31 178 | 11/1995 |
| WO | WO 97/18 839 | 5/1997 |

OTHER PUBLICATIONS

Chemical Abstracts, vol. 125, No. 26,Dec. 23, 1996, p. 708, column 1, abstract No. 338841t, deChasteigner, S. et al., "Comparative study of the association of itraconazole with colloidal drug carriers" .

* cited by examiner

*Primary Examiner*—José G Dees
*Assistant Examiner*—Frank Choi
(74) *Attorney, Agent, or Firm*—Fish & Richardson P.C.

(57) ABSTRACT

The particle diameter of itraconazole, insoluble drug, is reduced and crystallinity thereof is changed from crystalline into amorphous, increasing water solubility and a dissolution rate thereof. The improved itraconazole is applied to an oral adminstration drug.

7 Claims, 2 Drawing Sheets

INTRACONAZOLE EXHIBITING AN IMPROVED SOLUBILITY, A METHOD OF PREPARING THE SAME AND A PHARMACEUTICAL COMPOSITION FOR ORAL ADMINISTRATION COMPRISING THE SAME

CROSS REFERENCE TO RELATED APPLICATION

This application is a 371 of PCT/KR98/00164, filed Jun. 16, 1998.

This application is based on application No. 97-24938 filed in the Korean Industrial Property Office on June 16, 1997, the content of which is incorporated hereinto by reference.

BACKGROUND OF THE INVENTION (a) Field of the Invention

The present invention relates to an itraconazole and, more particularly, to an itraconazole exhibiting an improved solubility, a method of preparing the same and a pharmaceutical composition comprising the same.

(b) Description of the Related Art

Because the water-solubility of an azole-type antifungal agent such as itraconazole is low, bioavailability of a drug including the azole-type antifungal agent is low, when the drug is orally administered to a patient. Various studies have been attempted to increase the water solubility and bioavailability of the azole-type antifungal agent. The solubility and bioavailability of the compounds can be increased by complexation with cyclodextrins or derivatives thereof as described in WO 85/02767 and U.S. Pat. No. 4,764,604. WO 94/05263 reports a method of formulating a bead type drug by using a soluble polymer and the itraconazole.

As the azole-type antifungal agent, itraconazole has been widely used. Itraconazole has a molecular formula of $C_{35}H_{38}Cl_2N_8O_4$ and molecular weight of 705.64. Itraconazole is powder showing light yellow color end insoluble in water (solubility of less than 1 $\mu$g/ml), slightly soluble in alcohol (300 $\mu$g/ml) and soluble in methylene chloride (239 mg/ml). Itraconazole is a weak basic compound (pKa=3.7) and is only ionized at low pH, such as in gastric juice. The log partition coefficient of itraconazole in a system of n-octanol and an aqueous buffer solution of pH 8.1 is 5.66, indicative of very high lipophilicity. This property may influence its plasma protein binding and tissue distribution. Furthermore, it has been known that itraconazole is a broad spectrum antifungal compound developed for oral, parenteral and/or topical use and is disclosed in U.S. Pat. No. 4,267,179.

SUMMARY OF THE INVENTION

It is an object of the present invention to provide itraconazole exhibiting an improved solubility by reducing particle size and changing the crystallinity thereof from crystalline into amorphous.

It is another object to provide a method of preparing the itraconazole by dissolution-induced drying.

It is another object to provide a pharmaceutical composition for oral administrating the itraconazole.

These and other objects may be achieved by itraconazole exhibiting an improved solubility, wherein a particle diameter of the itraconazole is about 0.5 to about 10 $\mu$m and has an amorphous form.

The present invention further includes a method of preparing itraconazole exhibiting the improved solubility. The method includes the steps of dissolving itraconazole in an organic solvent and dissolution-induced drying the mixture.

The present invention further includes a pharmaceutical composition including the itraconazole exhibiting the improved solubility as an active ingredient.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing, wherein.

DETAILED DESCRIPTION OF THE INVENTION

Figure 1:
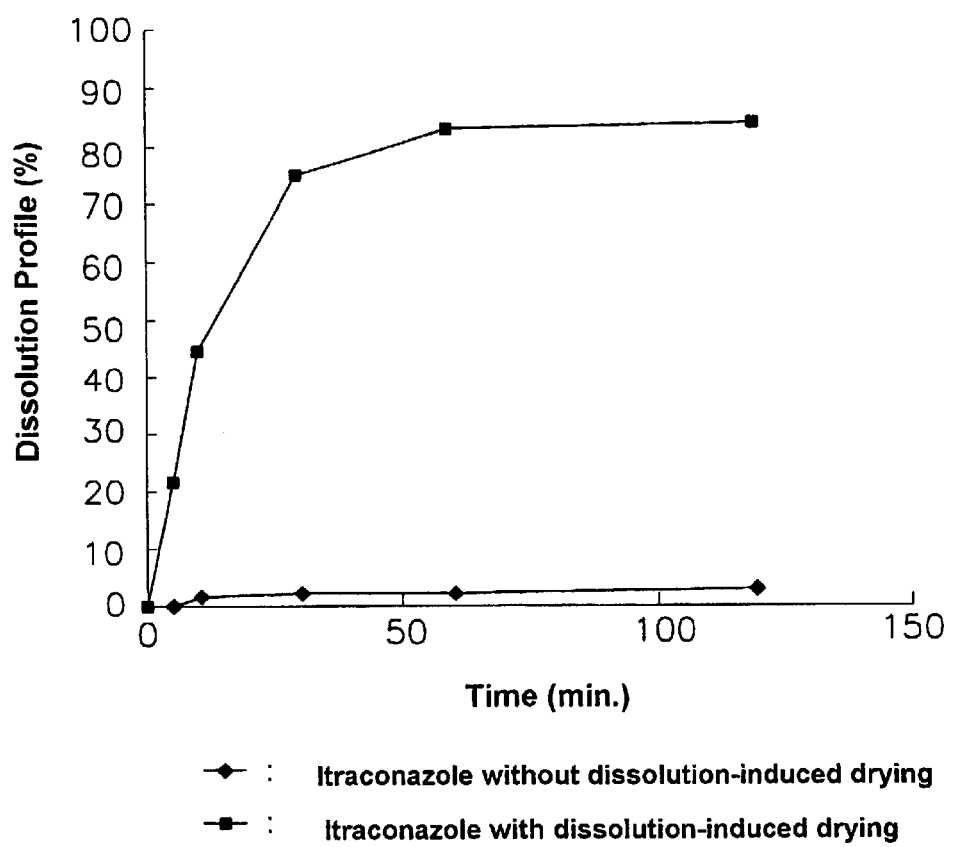
FIG. 1 is a graph showing dissolution profile of itraconazole with and without dissolution-induced drying according to time.

For absorbing a solid drug into a systemic circulation via epithelial cells, the solid drug should be soluble in water. Because a water-insoluble drug is slowly dissolved from a solid formulation, the drug dissolution step is rate-limiting step in absorbing the drug. Thus, the potency of the drug and on set time, the potency duration time depend on the dissolution rate of the drug.

The concentration of a drug in blood depends on the absorption and elimination rates thereof. Therefore, as the dissolution rate of the drug decreases, the absorption rate of the drug is reduced. As a result, although the total amount of drug absorbed into a human body is constant, time for reaching effective concentration thereof in blood is getting longer and maximum concentration thereof in blood decreases. Therefore, bioavailability and solubility of water-insoluble drugs decreases.

In order to solve these disadvantages and increase bioavailability and solubility, it is required to increase the dissolution rate of the water-insoluble drugs. For that purpose, particle size of the drug is reduced, or polymorphism, complex form, amorphous form, solid solution, co-melting mixture, conjugated compound, solvated compound of the drug and general drug additives are used.

The present invention provides an improved itraconazole having reduced particle size and modified crystalline characteristics from crystalline into amorphous. The improved itraconazole exhibits good water solubility, thereby increasing the bioavailability.

A method of preparing the improved itraconazole will be now illustrated in more detail.

Itraconazole is dissolved in an organic solvent and dissolution-induced dried to obtain powder of itraconazole. An amount of itraconazole in the organic solvent is 2 to 6 wt % and preferably, 4 wt %. It is preferred that the organic solvent is methylene chloride which is a good solvent for itraconazole. The dissolution-induced drying step is performed with a spray drier, a centrifugal granulator or fluid-bed granulator. In the dissolution-induced drying step, a carrier, for example, lactose or other pharmaceutical excipients may be used. The pharmaceutical excipients may be include a binder, a disintergrant, an agent for increasing viscosity, a lubricant, a stabilizer, a surfactant, a preservative, an electrolyte, a composite and a complex compound or another active material.

In the preparing step, it is important to control a dissolution-induced drying rate. If dissolution-induced drying rate is extremely slow, the solvent is too fast evaporated so that a large amount of drug is loss. Contrarily, if dissolution-induced drying rate is fast, microparticles are entangled with another, prior to evaporation, enlarging the particle size. It is preferred that the dissolution-induced drying rate is controlled to be slow initially and then controlled to gradually increase.

The particle size depends on an atomizing air pressure as well as the dissolution-induced drying rate. Low atomizing air pressure results in the formulation of larger droplets and increased tendency toward agglomeration. High atomizing air pressure could conceivably carry the risk of dissolution-induced drying of the drug solution, but this was found not to be a problem. Consequently, atomizing air pressure may be set at nearly maximum level.

The physical changes of itraconazole may be confirmed by differential scanning calorimeter (DSC) and x-ray crystallography.

Itraconazole prepared by method of the present invention has a particle diameter of about 0.5 to about 10 $\mu$m and an average particle diameter of about 3.7 $\mu$m. The itraconazole may include a trace of particles with diameter of below 0.5 $\mu$m.

The itraconazole of the present invention may be used as an active ingredient for a pharmaceutical composition for oral administration.

The pharmaceutical composition further includes vehicle such as lactose as carrier, or other pharmaceutical excipients.

The pharmaceutical excipients may be include a binder, a disintegrant, an agent for increasing viscosity, a lubricant, a stabilizer, a surfactant, a preservative, an electrolyte, a composite and a complex compound or another active material.

Itraconazole of the present invention is applied to various types of a drug for oral administration. The various type of the drug are a tablet, a capsule, a granule and a fine-granule. One tablet or one capsule may include 50 mg to 100 mg of itraconazole.

The present invention is further explained in more details with reference to the following examples. The examples is not intended to limit the present invention.

EXAMPLE 1

12g of itraconazole was accurately weighed and dissolved in 200 ml of methylene chloride. The mixture was then dissolution-induced dried by using a spray-drier to obtain powder of itraconazole. The air temperature in inlet and outlet of the spray drier were controlled to be 80±5° C. and 60±5° C., respectively. The dissolution-induced drying rate was controlled to be slow initially and then controlled to gradually increase.

EXAMPLE 2

12g of itraconazole was accurately weighed and dissolved in 200 ml of methylene chloride. The mixture was then dissolution-induced dried by using a fluid-bed granulator. The air temperatures in inlet and outlet of the fluid-bed granulator were controlled to be 80±5° C. and 60±5° C., respectively. The dissolution-induced drying rate was controlled to be slow initially and then controlled to gradually increase During the dissolution-induced drying, a drying step was performed to completely evaporate the solvent.

EXAMPLE 3

12g of Itraconazole was accurately weighed and dissolved in 200 ml of methylene chloride. The mixture was then dissolution-induced dried by using a C/F granulator to prepare powder thereof. The air temperatures in inlet and outlet of the C/F granulator were controlled to be 80±5° C. and 60±5° C., respectively. The rotation speed of rotor in the C/F granulator was 200 rpm. The dissolution-induced drying rate was controlled to be slow initially, and then controlled to gradually increase. During the dissolution-induced drying, a drying step was performed to completely evaporate the solvent.

EXAMPLE 4

Tablet preparation

Itraconazole prepared from Example 1, lactose, calcium carboxymethylcellulose and hydroxypropylmethylcellulose were uniformly mixed. The mixture was dry-granulated by a roller compactor to prepare granules. The granules were mixed with magnesium stearate as lubricant. The mixture was tableted to prepare a tablet. The amounts of each of the components in one tablet were as follows.

| | |
|---|---|
| Itraconazole | 100 mg |
| lactose | 279 mg |
| calcium carboxymethylcellulose | 250 mg |
| magnesium stearate | 1 mg |
| hydroxypropylmethylcellulose | 20 mg |

EXAMPLE 5

Capsule preparation

Itraconazole prepared from Example 1, lactose, calcium carboxymethylcellulose and hydroxymethylcellulose were uniformly mixed. The mixture was dry-granulated by using a roller compactor to prepare granules. The granules were mixed with magnesium stearate as lubricant and charged into a hard capsule No. 0. The amounts of each of the components were as follows:

| | |
|---|---|
| Itraconazole | 100 mg |
| lactose | 179 mg |
| calcium carboxymethylcellulose | 200 mg |
| magnesium stearate | 1 mg |
| hydroxypropylmethylcellulose | 20 mg |

EXPERIMENT 1

Determination of solubility

Excess of itraconazole from Example 1 and conventional itraconazole prepared without dissolution-induced drying were added to artificial gastric juice of pH 1.2 and shaken at 37° C. for 2 hours, respectively. Each of the mixture were filtered through a membrane filter with pore diameter of 0.45 tan and each of the filtrate was subjected to high-performance liquid chromatography, thereby obtaining gastric juice solubility.

The results are shown in Table 1.

TABLE 1

Solubility (37° C., 2 hours, pH 1.2)

|  | μg/ml |
|---|---|
| The conventional itraconazole without dissolution-induced drying | 3.5 |
| Itraconazole of Example 1 | 218.6 |

As shown in Table 1, solubility of itraconazole of the Example 1 is 62 times larger than that without dissolution-induced drying. Therefore, it is shown that solubility of itraconazole of the present invention significantly increases with compared to the conventional itraconazole without dissolution-induced drying.

EXPERIMENT 2

Determination of particle size

Itraconazole powder prepared from Example 1 and the conventional itraconazole powder without dissolution-induced drying were uniformly distributed in liquid paraffin and particle diameter thereof were determined, respectively. The results are shown in Tables 2 to 4.

TABLE 2

The conventional Itraconazole without dissolution-induced drying

| Particle size (μm) | Distribution ratio of particle (%) | Accumulated amount (wt %) |
|---|---|---|
| ~5 | 2.4 | 2.4 |
| 5 ~ 15 | 21.8 | 24.2 |
| 15 ~ 17.5 | 18.4 | 40.6 |
| 17.5 ~ 20 | 9.9 | 50.5 |
| 20 ~ 30 | 23.9 | 74.4 |
| 30 ~ 35 | 8.0 | 82.4 |
| 35 ~ 40 | 8.1 | 90.5 |
| 40 ~ 52.5 | 9.5 | 100.0 |

TABLE 3

Itraconazole of Example 1

| Particle size (μm) | Distribution ratio of particle (%) | Accumulated amount (wt %) |
|---|---|---|
| ~0.5 | 2.4 | 2.4 |
| 0.5 ~ 1.25 | 25.8 | 28.2 |
| 1.25 ~ 2.5 | 24.0 | 52.2 |
| 2.5 ~ 5 | 34.2 | 86.4 |
| 5 ~ 7.5 | 12.2 | 98.6 |
| 7.5 ~ 10 | 1.4 | 100.0 |

TABLE 4

Average particle diameter

|  | μm |
|---|---|
| The conventional itraconazole without dissolution-induced drying | 24.5 |
| itraconazole of Example 1 | 3.7 |

The average diameter of itracoazole particle of the present invention is 7 times smaller than that without dissolution-induced drying

EXPERIMENT 3

Dissolution rate test

The dissolution rate test on the itraconazole tablet prepared from Example 4 and a conventional itraconazole tablet without dissolution-induced drying were performed.

The itraconazole tablet prepared from Example 4 and the conventional itraconazole tablet were respectively added to artificial gastric juice of pH 1.2 as an eluting solvent. While keeping at 37° C., 5ml of the sample was taken from the mixture after 5, 10, 30, 60 and 120 minutes, respectively. Each of the samples were filtered by using a filter of 0.45 micrometers and each of the filtrate were subjected to high-performance liquid chromatography. The results are shown in FIG. 1.

As shown in FIG. 1, dissolution rate and solubility of itraconazole with dissolution-induced drying is greatly enhanced with compared to itraconazole without dissolution-induced drying.

EXPERIMENT 4

The physical property test

Figure 2:
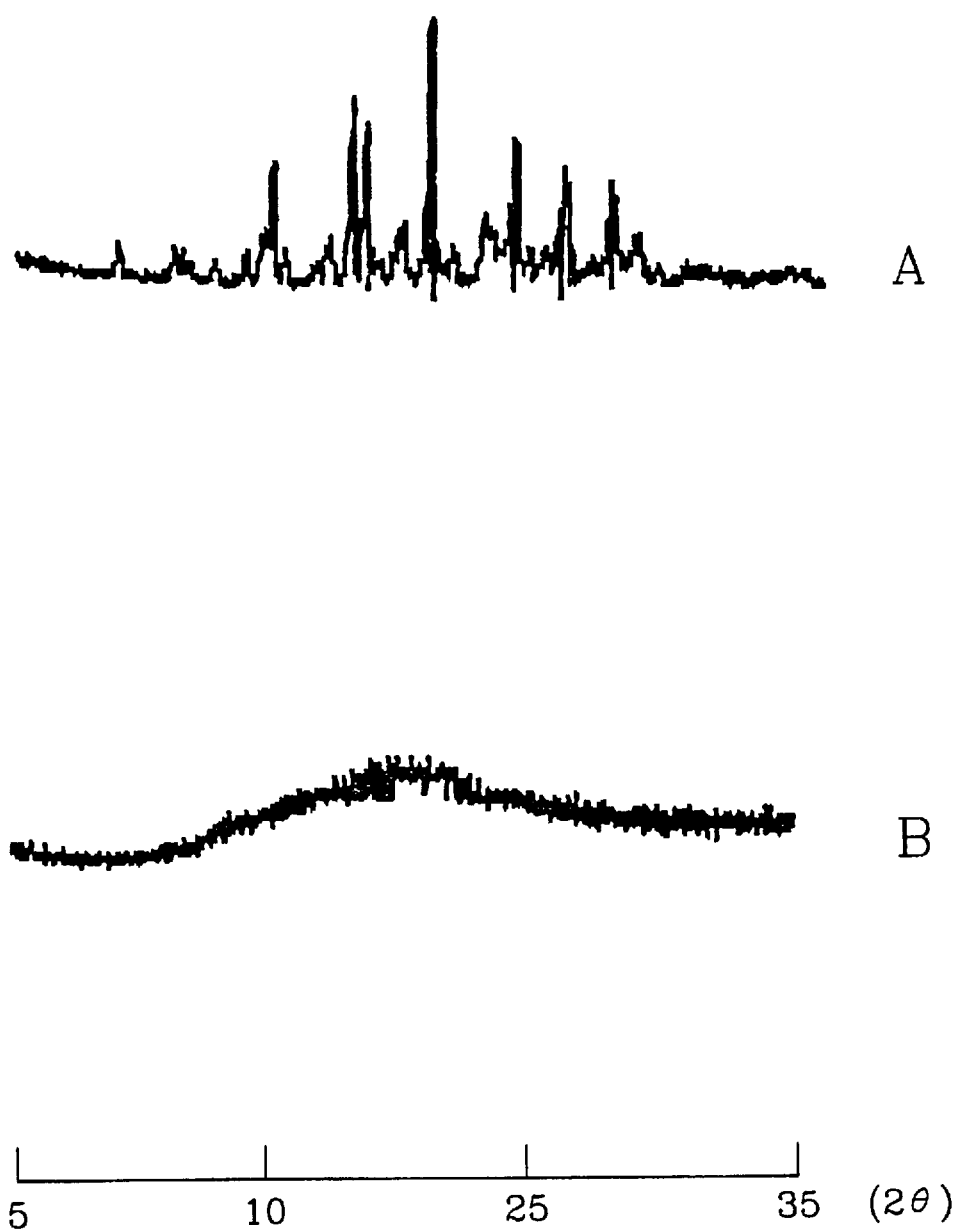
FIG. 2 is a graph showing X-ray diffraction patterns of itraconazole is with and without dissolution-induced drying.

The physical changes of itraconazole was confirmed by x-ray diffraction and result are shown in FIG. 2. In FIG. 2, pattern A shows x-ray diffraction pattern of itraconazole without dissolution-induced drying. Pattern B shows x-ray diffraction pattern of itraconazole with dissolution-induced drying. As shown in FIG. 2, itraconazole without dissolution-induced drying has an crystalline form and itraconazole with dissolution-induced drying has an crystalline form.

As described above, the present invention is capable of increasing solubility of itracobazole being insoluble drug and a dissolution rate and itraconazole of the present invention is applied to solid preparation.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method of preparing itraconazole in an amorphous form, comprising the steps of:

dissolving itraconazole in an organic solvent; and dissolution-induced drying the mixture with a spray drier, fluid-bed granulator, or a centrifugal granulator, at a drying rate controlled to be slow initially and then gradually increase, under high atomizing air pressure to obtain itraconazole in an amorphous form exhibiting an improved bioavailability, and having a particle diameter of 0.5 to 10 μm.

2. The method of claim 1, wherein the average particle diameter of itraconazole is about 3.7 μm.

3. An itraconazole produced by the method of claim 1, wherein the intraconazole is in an amorphous form, exhibits an improved bioavailability, and has a particle diameter of 0.5 to 10 μm.

4. The itraconazole of claim 3, said itraconazole having an average particle diameter of about 3.7 μm.

5. A pharmaceutical composition for oral administration, comprising itraconazole in an amorphous form, exhibiting an improved bioavailability and having a particle diameter of 0.5 to 10 μm, wherein the itraconazole is prepared according to the method of claim 1.

6. The pharmaceutical composition of claim 5, wherein the itraconazole has an average particle diameter of about 3.7 μm.

7. The pharmaceutical composition of claim 5, further comprising a vehicle or a pharmaceutical excipient.

* * * * *